United States Patent
Kaneko et al.

(10) Patent No.: US 6,982,076 B2
(45) Date of Patent: Jan. 3, 2006

(54) NAIL CARE PRODUCTS

(75) Inventors: Katsuyuki Kaneko, Yokohama (JP);
Hirotaka Takada, Yokohama (JP);
Tsuneo Suhara, Yokohama (JP);
Yoshikazu Soyama, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 590 days.

(21) Appl. No.: 10/182,151

(22) PCT Filed: Nov. 29, 2001

(86) PCT No.: PCT/JP01/10426

§ 371 (c)(1),
(2), (4) Date: Oct. 16, 2002

(87) PCT Pub. No.: WO02/43676

PCT Pub. Date: Jun. 6, 2002

(65) Prior Publication Data

US 2004/0081630 A1 Apr. 29, 2004

(30) Foreign Application Priority Data

Nov. 29, 2000 (JP) ...................................... 2000-362581

(51) Int. Cl.
*A61K 7/04* (2006.01)

(52) U.S. Cl. ......................................... 424/61; 424/401
(58) Field of Classification Search .................. 424/61, 424/401
See application file for complete search history.

(56) References Cited

FOREIGN PATENT DOCUMENTS

| JP | 54-129137 | 10/1979 |
|----|-----------|---------|
| JP | 61-246113 | 11/1986 |
| JP | 05-213719 | 8/1993 |
| JP | 06-279239 | 10/1994 |

*Primary Examiner*—Thurman K. Page
*Assistant Examiner*—Sharon Howard
(74) *Attorney, Agent, or Firm*—Snider & Associates; Ronald R. Snider

(57) ABSTRACT

The present invention relates to a nail-care composition.

It is an object of the present invention to provide a solvent-based nail-care composition which can be easily applied to nails, provides a film (coating film) on the nail with excellent strength and gloss, and generates a coating film that is difficult to peel off over time and free from loss of gloss.

The means used to meet the objective is a nail-care composition comprising (a) nitrocellulose, (b) neopentyl glycol trimellitate adipate polyester resin, (c) one, two, or more members selected from the group consisting of alkyl methacrylate-alkyl acrylate copolymers, sucrose benzoate, and a polymer compound having a glass transition temperature of 50–80° C., and (d) a solvent.

The present invention provides a solvent-based nail-care composition which is easy to apply, excellent in the strength of film(coating film) on the nail and gloss, difficult to peel off over a period of time, and free from the loss of gloss.

11 Claims, No Drawings

NAIL CARE PRODUCTS

TECHNICAL FIELD

The present invention relates to a nail-care composition. It further relates to a solvent-based nail-care composition which is easily applied to nails, provides a film (coating film) on the nail with excellent strength and gloss, and generates a coating film which is difficult to peel off over time and free from loss of gloss.

PRIOR ART

Solvent-based nail-care compositions have conventionally been formulated with a variety of resins for improving properties such as the ease of application, gloss, peeling off characteristics, and the like. Among them, there are many technologies of formulating nitrocellulose as a film-forming agent: for example, Japanese Patent Laid-Open Publication No. S61-246113 discloses a nail-care composition with improved peeling off characteristics and the like by formulating in a nitrocellulose-containing nail-care composition, a combination of a modified alkyd resin such as a glycidyl versatate ester modified-alkyd resin and sucrose benzoate. Japanese Patent Laid-Open Publication No. H5-213719 discloses a nail-care composition that improves on the art described in the above Japanese Patent Laid-Open Publication No. S61-246113 by incorporating a silicone-based grafted copolymer.

There have also been a number of developments of film-forming agents replacing nitrocellulose: Japanese Patent Laid-Open Publication No. S54-129137 discloses a nail-care composition containing, as a film forming agent, a blend of acrylic resins (a preferred number average molecular weight of 15,000–200,000) from a methacrylate ester copolymer comprised of 35–65% by weight of methyl methacrylate and/or ethyl methacrylate and 65–35% by weight of propyl methacrylate and/or butyl methacrylate and a methacrylate ester/acrylate ester copolymer comprised of 50–85% by weight of methyl methacrylate and/or ethyl methacrylate and 50–15% by weight of methyl acrylate and/or ethyl acrylate. Japanese Patent Laid-Open Publication No. H6-279239 discloses a nail-care composition using as a film-forming agent, a copolymer having a molecular weight of 10,000–70,000 comprised of 20–85% by weight of styrene and/or methyl methacrylate, 5–60% by weight of an alkyl acrylate ester (the alkyl chain length of 1–8), and 7–30% by weight of acrylic acid.

Thus, research and development has been intense on products aimed at improving the properties required of nail-care compositions. In particular, with an increasing demand for an even higher quality nail-care composition by consumers, along with diversification of preferences, there are ever increasing demands for nail-care composition having many excellent properties combined therein.

It is an object of the present invention, in response to the above state of art, to provide a solvent-based nail-care composition which is easily applied to nails, provides a film (coating film) on the nail with excellent strength and gloss, and generates a coating film that is difficult to peel off over time and free from loss of gloss.

DISCLOSURE OF THE INVENTION

As a result of their extensive studies of a way to solve the above problem, the present inventors discovered that the above problems can be overcome by formulating in combination a specific polyester resin along with a specific acrylic resin, sucrose derivative, or a polymer compound having a specific glass transition temperature in a nitrocellulose-containing solvent-based nail-care composition, which has resulted in the completion of the present invention.

That is, the present invention is a nail-care composition comprising (a) nitrocellulose, (b) neopentyl glycol trimellitate adipate polyester resin, (c) one, two, or more members selected from the group consisting of alkyl methacrylate-alkyl acrylate copolymers, sucrose benzoate, and a polymeric compound having a glass transition temperature of 50–80° C., and (d) a solvent. It is preferred for the neopentyl glycol trimellitate adipate polyester resin to have an acid value of 10–30 mgKOH/g. The composition within this range can exhibit a further substantial effect of preventing the coating film from peeling over time.

It is preferred for the alkyl group in the alkyl methacrylate and alkyl acrylate constituting the alkyl methacrylate-alkyl acrylate-containing copolymer to have 1–8 carbon atoms. Within this range, the coating film strength and gloss development effects can be made more substantial.

The alkyl methacrylate-alkyl acrylate-containing copolymer preferably has a weight average molecular weight of 1,000–9,000. Polymers within this range can provide excellent coating film strength and gloss as well as the excellent effect of preventing the coating film from peeling off over time. The ease of application will also be excellent.

EMBODIMENTS OF THE PRESENT INVENTION

Hereafter, embodiments of the present invention are described in detail.

(a) Component nitrocellulose may be one or a combination of two or more types from those conventionally used and known in the art. Nitrocelluloses, for example, include nitrocellulose 1/16 sec, nitrocellulose 1/8 sec, nitrocellulose 1/4 sec, nitrocellulose 1/2 sec, nitrocellulose 1 sec, nitrocellulose 2 sec, nitrocellulose 7 sec, nitrocellulose 20 sec, and the like. From among these, nitrocellulose 1/16 sec, nitrocellulose 1/8 sec, nitrocellulose 1/4 sec, and nitrocellulose 1/2 sec are preferred.

The amount of nitrocellulose formulated should be determined in consideration of the other formulated components, but it should preferably be 5–25% be weight of the entire weight of the nail-care composition as wetted with 30% by weight isopropyl alcohol (hereafter, 30% IPA). At a level below 5% by weight there is the danger of losing the gloss over time, but a level exceeding 25% by weight might make the coating difficult. A particularly preferred range is 10–20% by weight. At a level within this range, the effect of the present invention can be fully developed.

(b) Component neopentyl glycol trimellitate adipate polyester resin is a polyester obtained by treating trimellitic acid, neopentyl glycol, and adipic acid. Different ratios of the 3 components will provide polymers with different physical properties, but the preferred product has an acid value of 10–30 mg KOH/g. Within this range, the composition can provide a greater effect of preventing the coating film from peeling off. The neopentyl glycol trimellitate adipic polyester resin in this invention is hereafter called the "adipate polyester resin." For the adipate polyester resin component, it is permissible, for example, to use a commercially available product under the designation "UNIPLEX 670-P [(Manufactured by UNITEX Chemical Corporation).

The amount of the adipate polyester resin to be formulated is determined in consideration of other formulated components, but it should preferably be 3.0–20.0% by weight of the entire nail-care composition. A level less than 3.0% by weight tends to adversely affect the effect on peeling over time while a level exceeding 20.0% by weight tends to adversely affect the gloss and the strength. A particularly preferred range is 5–15% by weight. Within this range, the effect of the present invention can be fully developed.

The alkyl methacrylate and alkyl acrylate constituting the (c) component alkyl methacrylate-alkyl acrylate copolymer should have alkyl groups preferably containing 1–8 carbon atoms. Within this range, the coating film strength and gloss development effect can be more fully developed.

The alkyl methacrylates are, for example, methyl methacrylate, ethyl methacrylate, propyl methacrylate, butyl methacrylate, octyl methacrylate, 2-ethylhexyl methacrylate, and the like, the alkyl acrylates are, for example, methyl acrylate, ethyl acrylate, propyl acrylate, butyl acrylate, octyl acrylate, 2-ethylhexyl acrylate, and the like. Monomers other than the alkyl methacrylate and alkyl acrylate constituting the alkyl methacrylate-alkyl acrylate containing copolymers include styrene, methacrylic acid, acrylic acid, acrylonitrile, and the like, but use of them is not necessarily required.

The alkyl methacrylate-alkyl acrylate containing copolymers are synthesized by a conventional manufacturing method. The copolymer is, for example, obtained by radical polymerization of monomers constituting the copolymer. Obviously, it is permissible to use a commercial copolymer which, for example, includes JONCRYL 611 (sold by Johnson Polymer Co., Ltd.) and the like. JONCRYL 611 is a polymeric compound having a glass transition temperature of 64° C. The alkyl methacrylate-alkyl acrylate copolymer may be formulated singly or as a combination of 2 or more.

The molecular weight of the alkyl methacrylate-alkyl acrylate-containing copolymer is preferably 1,000–20,000 in weight average molecular weight. In particular, a low molecular weight range of 1,000–9,000 is preferred for substantially attaining the effect of this invention. Within this range, the polymer will provide outstanding coating film strength and gloss as well as substantial effect of preventing coating film from peeling off over time.

The amount of the alkyl methacrylate-alkyl acrylate-containing copolymer to be formulated is determined by the physical properties of the copolymer and in relation to the other formulated components, but is should preferably be 1–25% by weight of the total weight of the nail-care composition. A level less than 1% by weight will cause the film strength to decrease, with the danger of a decrease in gloss over time, whereas a level exceeding 25% by weight tends to adversely affect the effect on peeling with time, along with the danger of making it difficult to apply. A particularly preferred range is 8–20% by weight. Within this range, the effect of this invention can be fully developed.

Sucrose benzoate, another component of (c) used in this invention, is one of the conventionally known nail-care resins. It is permissible to use a commercial sucrose benzoate which, for example, includes a product manufactured by Dai-Ichi Kogyo Seiyaku Co., Ltd under the trade name MONOPET SB and Sucrose benzoate (a product manufactured by Velsicol Chemical Corporation, USA) and the like. MONOPET SB (manufactured by Dai-Ichi Kogyo Seiyaku Co., Ltd.) is a polymeric compound having a glass transition temperature of 64° C.

The amount of sucrose benzoate formulated should be determined in relation to the other formulated components and is preferably in a range of 0.5–25% by weight of the total weight of the nail-care composition. A level less than 0.5% by weight will result in the danger of reducing the film strength and decreasing the gloss over time. A level exceeding 25% by weight tends to adversely affect the effect on peel over time, along with the danger of making the coating difficult. A further preferred range is 3–15% by weight. Within this range, the effect of this invention can be fully developed.

Another component of (c) in this invention is a polymeric compound having a glass transition temperature of 50–80° C. It is preferably a polymeric compound having a glass transition temperature of 55–75° C. Incidentally, the glass transition temperature is determined using a DSC instrument, (differential scanning calorimeter) (SSC5100), a product of Seiko Instrument Company) using a 10 mg sample at a heating rate of 5° C./minute over a range of –20° C.–120° C. and determining, from the chart obtained, the temperature at which the DSC peak begins to rise as the glass transition temperature. Among the (c) components mentioned above, there are included those with glass transition temperatures of 50–80° C., but it is permissible to use a polymeric compound outside of that range. A polymeric compound having a glass transition temperature of 50–80° C. is formulated singly or in combination of 2 or more.

The amount of a polymer having a glass transition temperature of 50–80° C. to be formulated is determined in relation to the other formulated components, but it is preferably in a range of 05–25% by weight of the total weight of the nail-care composition. A level less than 0.5% by weight will result in the danger of reduced film strength and a decrease in gloss over time, while a level exceeding 25% by weight tends to adversely affect the effect on peel over time, along with the danger of making the application difficult. A further preferred range is 3–15% by weight. Within this range, the effect of the present invention can be fully developed.

If (c) components, alkyl methacrylate-alkyl acrylate containing copolymer, sucrose benzoate, and a polymeric compound having a glass transition temperature of 50–80° C., are used as a mixture, the total weight of the three formulated should preferably be not more than 25% by weight.

(d) component solvents may be conventionally known esters, alcohols, hydrocarbon types, and the like. For example, they include methyl acetate, ethyl acetate, butyl acetate, amyl acetate, ethyl lactate, butyl lactate, ethyl alcohol, isopropyl alcohol, butyl alcohol, toluene, isobutyl acetate, propyl acetate, isopropyl acetate, propyl alcohol, and the like. In particular, it is preferred to use butyl acetate, ethyl acetate, isopropyl alcohol, butyl alcohol, ethyl alcohol, and the like. The solvent may be used singly or in combination of 2 or more.

The amount of the solvent formulated differs, depending upon its behavior in use, color, and the like, but it is generally about 50–85% by weight of the total nail-care composition.

In addition to the above components, the nail-care composition of this invention may be formulated optionally, to the extent of not adversely affecting the effect of this invention, with ingredients which are generally formulated in nail-care compositions, such as resins other than the above essential resin components of this invention, plasticizers, pigments, fragrances, dyes, pearlescent agent, lamellas, humectants, UV absorbers, delusterant, fillers, surfactants, viscosity improvers, metal soaps, clay modifiers such as organic acids, and the like. Among these, it is preferred to incorporate a plasticizer in the nail-care composition of this invention for improving coating film properties such as peeling off, coating film strength, and the like.

Plasticizers used may be selected from known types such as camphor, phthalate esters, and citrate esters. For example, dibutyl phthalate, dioctyl phthalate, tributyl citrate, acetyltriethyl citrate, acetyltributyl citrate, and the like can be mentioned. One, two, or more may be selected from these without limitation. The amount formulated is in general, 1–10% by weight of the total nail-care composition.

Resins other than the essential resins of this invention include modified alkyd resins such as glycidyl vasatate, toluene sulfonamide resin, sucrose acetate-isobutyrate ester, a silicone-grafted copolymer, and the like. Formulating these resins can further enhance the peel characteristics and the absence of the feeling of compression to the nail without adversely affecting the ease of coating, gloss, and the like.

These resins are preferably formulated in an amount of 0.1–10% by weight of the total nail-care composition.

The solvent-based nail-care composition of this invention includes, but not limited to, a broad range of nail coating agents commonly used in the cosmetic industry as manicures and nail-careing products, such as base coats, nail enamels, top coats (over coats) and nail care products such as nail guards and the like, without being limited to these examples.

The present invention is further explained in details based on working examples of this invention. Incidentally, the amount formulated is expressed in percent by weight.

Prior to the explanation of the examples of this invention, the various evaluation methods used in these examples are explained as bellow.

[Ease of Application]

Each sample filled in a 10 ml glass bottle having an attached brush was applied by a 20-member professional panel to individual's nails (one coat, two coats); ease of application in coating was rated in 5 grades. Individual's grade points were totaled. A rating standard will be summarized later.

| (Rating Points) | |
| --- | --- |
| 5 Points: | Very smooth application |
| 4 Points: | Smooth application |
| 3 Points: | Ordinary level |
| 2 Points: | Difficulty in application |
| 1 Point: | Much difficulty in application |

[Coating Film Strength]

Each sample filled in a 10 ml glass bottle having an attached brush was applied by a 20-member professional panel to individual's nails; the extent of chipping of the nail-coating film after spending 4 days in living environmental conditions was rated in 5 grades. Individual's grade points were totaled. A rating standard will be summarized later.

| (Rating Points) | |
| --- | --- |
| 5 Points: | Very difficult to chip |
| 4 Points: | Difficult to chip |
| 3 Points: | Ordinary level |
| 2 Points: | Easy to chip |
| 1 Point: | Very easy to chip |

[Gloss]

Each sample filled in a 10 ml glass bottle having an attached brush was applied by a 20-member professional panel to individual's nails; the gloss of the coating film after spending 4 days in living environmental conditions was rated in 5 grades. Individual's grade points were totaled. A rating standard will be summarized later.

| (Rating Points) | |
| --- | --- |
| 5 Points: | Very glossy |
| 4 Points: | Glossy |
| 3 Points: | Ordinary level |
| 2 Points: | Not glossy |
| 1 Point: | Very non-glossy |

[Peeling Off Over a Period of Time]

Each sample filled in a 10 ml glass bottle with an attached brush was applied by a 20-member professional panel to individual's nails; the extent of the peeling off of nail-coating films after spending 4 days in living environmental conditions was rated in 5 grades. Individual's grade points were totaled. A rating standard will be summarized later.

| (Rating Points) | |
| --- | --- |
| 5 Points: | Very difficult to peel |
| 4 Points: | Difficult to peel |
| 3 Points: | Regular |
| 2 Points: | Easy to peel |
| 1 Point: | Very easy to peel |

| (Evaluation Standards for the Above Test Items) | |
| --- | --- |
| ⊚ | A point total is 90 points or greater. |
| ○ | A point total is 70 points or higher but less than 90 points. |
| □ | A point total is 50 points or higher but less than 70 points |
| Δ | A point total is 50 points or higher but less than 70 points |
| X | A point total is less than 30 points. |

EXAMPLES 1–45

Comparative Examples 1–4

Nail-care compositions were prepared by the usual method according to the recipes listed in Tables 1–10 and were individually evaluated by the above evaluation methods in terms of ease of application, coating film strength, gloss, and peeling off over time. The results are respectively given in Tables 1–10.

TABLE 1

| | Examples | | | Comparative Ex. | | | |
| --- | --- | --- | --- | --- | --- | --- | --- |
| | 1 | 2 | 3 | 1 | 2 | 3 | 4 |
| Nitrocellulose ¼ sec (30% IPA) (a) | 12 | 12 | 12 | 12 | 12 | 12 | 12 |
| Adipate polyester resin (b) | 10 | 10 | 10 | 10 | — | — | — |
| Methyl methacrylate-butyl acrylate Copolymer (c) | 10 | — | — | — | 10 | — | — |

TABLE 1-continued

|  | Examples | | | Comparative Ex. | | | |
| --- | --- | --- | --- | --- | --- | --- | --- |
|  | 1 | 2 | 3 | 1 | 2 | 3 | 4 |
| Sucrose benzoate (c) | — | 10 | — | — | — | 10 | — |
| JONCRYL 611 (c) | — | — | 10 | — | — | — | 10 |
| Acetyltriethyl citrate | 5 | 5 | 5 | 5 | 5 | 5 | 5 |
| n-Butyl alcohol | 1 | 1 | 1 | 1 | 1 | 1 | 1 |
| Ethyl acetate | 20 | 20 | 20 | 20 | 20 | 20 | 20 |
| n-Butyl acetate | Bal* | Bal | Bal | Bal | Bal | Bal | Bal |
| Organically modified clay mineral | Opt* | Opt | Opt | Opt | Opt | Opt | Opt |
| Pearlescent agent | 2 | 2 | 2 | 2 | 2 | 2 | 2 |
| Pigment | 1 | 1 | 1 | 1 | 1 | 1 | 1 |
| Ease of application | ◎ | ◎ | ◎ | ○ | Δ | Δ | Δ |
| Coating film strength | ◎ | ◎ | ◎ | Δ | ○ | ○ | ○ |
| Gloss |  |  |  |  |  |  |  |
| 10 min. later | ◎ | ◎ | ◎ | Δ | ○ | ○ | ○ |
| 4 days later | ○ | ○ | ○ | Δ | □ | □ | □ |
| Peeling off over time | ◎ | ◎ | ◎ | ○ | X | X | X |

*Bal (Balance);
Opt (Optimum)

In Table 1, the adipate polyester resin was UNIPLEX 670-P. The methyl methacrylate-butyl acrylate copolymer had a weight average molecular weight of 8,100.

Table 1 clearly shows that Example 1, a formulation of nitrocellulose ¼ second, adipate polyester resin, and methyl methacrylate-butyl acrylate copolymer: Example 2, a formulation of nitrocellulose ¼ second, adipate polyester resin, and sucrose benzoate; and Example 3, a formulation of nitrocellulose ¼ second, adipate polyester resin, and JONCRYL 611 are all outstanding in every item: ease of application, coating film strength, gloss, and peeling off over time.

On the other hand, Comparative Example 1, a formulation with no (c) component is shown to have insufficient coating film strength and gloss. Comparative Examples 2, 3, and 4, formulations lacking (b) component, adipate polyester resin, are shown to be particularly insufficient in ease of coating and peeling off over time.

TABLE 2

|  | Examples | | | |
| --- | --- | --- | --- | --- |
|  | 4 | 5 | 6 | 7 |
| Nitrocellulose ¼ sec (30% IPA) (a) | 5 | 10 | 20 | 25 |
| Adipate polyester resin (b) | 10 | 10 | 10 | 10 |
| Methyl methacrylate-butyl acrylate Copolymer (c) | 10 | 10 | 10 | 10 |
| Acetyltriethyl citrate | 5 | 5 | 5 | 5 |
| n-Butyl alcohol | 1 | 1 | 1 | 1 |
| Ethyl acetate | 20 | 20 | 20 | 20 |
| n-Butyl acetate | Bal | Bal | Bal | Bal |
| Organically modified clay mineral | Opt | Opt | Opt | Opt |
| Pearlescent Agent | 2 | 2 | 2 | 2 |
| Pigment | 1 | 1 | 1 | 1 |
| Ease of Application | ◎ | ◎ | ◎ | ○ |
| Coating film strength | ○ | ◎ | ◎ | ◎ |
| Gloss |  |  |  |  |
| 10 min. later | ○ | ◎ | ◎ | ◎ |
| 4 days later | ○ | ○ | ○ | ○ |
| Peeling off over time | ○ | ◎ | ◎ | ○ |

In Table 2, the adipate polyester resin was UNIPLEX 670-P. The methyl methacrylate-butyl acrylate copolymer had a weight average molecular weight of 8,100.

Table 2 clearly shows that excellent effects are obtained when the amount of nitrocellulose formulated is in a range of 5–25% by weight. It particularly shows that a range of 10–20% by weight is preferred.

TABLE 3

|  | Examples | | | |
| --- | --- | --- | --- | --- |
|  | 8 | 9 | 10 | 11 |
| Nitrocellulose ¼ sec (30% IPA) (a) | 5 | 10 | 20 | 25 |
| Adipate ester resin (b) | 10 | 10 | 10 | 10 |
| Sucrose benzoate (c) | 10 | 10 | 10 | 10 |
| Acetyltriethyl citrate | 5 | 5 | 5 | 5 |
| n-Butyl alcohol | 0.5 | 0.5 | 0.5 | 0.5 |
| Ethyl acetate | 20 | 20 | 20 | 20 |
| n-Butyl acetate | Bal | Bal | Bal | Bal |
| Organically modified clay mineral | Opt | Opt | Opt | Opt |
| Pearlescent agent | 2 | 2 | 2 | 2 |
| Pigment | 1 | 1 | 1 | 1 |
| Ease of application | ◎ | ◎ | ◎ | ○ |
| Coating film strength | ○ | ◎ | ◎ | ◎ |
| Gloss |  |  |  |  |
| 10 min. later | ○ | ◎ | ◎ | ◎ |
| 4 days later | ○ | ○ | ○ | ○ |
| Peeling off over time | ○ | ◎ | ◎ | ○ |

In Table 3, the adipate polyester resin was UNIPLEX 670-P. Table 3 clearly shows that excellent effect is obtained when the amount of nitrocellulose formulated is in a range of 5–25% by weight. It particularly shows that a range of 10–20% by weight is preferred.

TABLE 4

|  | Examples | | | |
| --- | --- | --- | --- | --- |
|  | 12 | 13 | 14 | 15 |
| Nitrocellulose ¼ sec (30% IPA) (a) | 5 | 10 | 20 | 25 |
| Adipate polyester resin (b) | 10 | 10 | 10 | 10 |
| JONCRYL 611 (c) | 10 | 10 | 10 | 10 |
| Acetyltriethyl citrate | 5 | 5 | 5 | 5 |
| n-Butyl alcohol | 0.5 | 0.5 | 0.5 | 0.5 |
| Ethyl acetate | 20 | 20 | 20 | 20 |
| n-Butyl acetate | Bal | Bal | Bal | Bal |
| Organically modified clay mineral | Opt | Opt | Opt | Opt |
| Pearlescent Agent | 2 | 2 | 2 | 2 |
| Pigment | 1 | 1 | 1 | 1 |
| Ease of application | ◎ | ◎ | ◎ | ○ |
| Coating film strength | ○ | ◎ | ◎ | ◎ |

TABLE 4-continued

|  | Examples | | | |
| --- | --- | --- | --- | --- |
|  | 12 | 13 | 14 | 15 |
| Gloss | | | | |
| 10 min. later | ○ | ◎ | ◎ | ◎ |
| 4 days later | ○ | ○ | ○ | ○ |
| Peeling off over time | ○ | ◎ | ◎ | ○ |

In Table 4, the adipate polyester resin was UNIPLEX 670-P. Table 4 clearly shows that excellent effects are obtained when the amount of nitrocellulose formulated is in a range of 5–25% by weight. It particularly shows that a range of 10–20% by weight is preferred.

TABLE 5

|  | Examples | | | | |
| --- | --- | --- | --- | --- | --- |
|  | 16 | 17 | 18 | 19 | 20 |
| Nitrocellulose ¼ sec (30% IPA) (a) | 12 | 12 | 12 | 12 | 12 |
| Adipate polyester resin (b) | 3 | 5 | 7 | 15 | 20 |
| Methyl methacrylate-butyl acrylate Copolymer (c) | 10 | 10 | 10 | 10 | 10 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 3 | 3 | 3 | 3 | 3 |
| Ease of application | ◎ | ◎ | ◎ | ◎ | ◎ |
| Coating film strength | ◎ | ◎ | ◎ | ◎ | ○ |
| Gloss | | | | | |
| 10 min. later | ◎ | ◎ | ◎ | ◎ | ○ |
| 4 days later | ○ | ○ | ○ | ○ | ○ |
| Peeling off over time | ○ | ◎ | ◎ | ◎ | ◎ |

In Table 5, the adipate polyester resin was UNIPLEX 670-P. The methyl methacrylate-butyl acrylate copolymer had a weight average molecular weight of 8,000.

Table 5 clearly shows that excellent effects are obtained if the amount of adipate polyester resin formulated is in a range of 3–20% by weight. It particularly shows that a range of 5–15% by weight is preferred.

TABLE 6

|  | Examples | | | | |
| --- | --- | --- | --- | --- | --- |
|  | 21 | 22 | 23 | 24 | 25 |
| Nitrocellulose ¼ sec (30% IPA) (a) | 12 | 12 | 12 | 12 | 12 |
| Adipate polyester resin (b) | 3 | 5 | 7 | 15 | 20 |
| Sucrose benzoate (c) | 10 | 10 | 10 | 10 | 10 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 1 | 1 | 1 | 1 | 1 |
| Ease of application | ○ | ◎ | ◎ | ◎ | ○ |
| Coating film strength | ◎ | ◎ | ◎ | ◎ | ○ |

TABLE 6-continued

|  | Examples | | | | |
| --- | --- | --- | --- | --- | --- |
|  | 21 | 22 | 23 | 24 | 25 |
| Gloss | | | | | |
| 10 min. later | ○ | ◎ | ◎ | ◎ | ◎ |
| 4 days later | ○ | ○ | ○ | ○ | ○ |
| Peeling off over time | ○ | ◎ | ◎ | ◎ | ◎ |

In Table 6, the adipate polyester resin was UNIPLEX 670-P. Table 6 clearly shows that excellent effects are obtained if the amount of adipate polyester resin formulated is in a range of 3–20% by weight. It particularly shows that a range of 5–15% by weight is preferred.

TABLE 7

|  | Examples | | | | |
| --- | --- | --- | --- | --- | --- |
|  | 26 | 27 | 28 | 29 | 30 |
| Nitrocellulose ¼ sec (30% IPA) (a) | 12 | 12 | 12 | 12 | 12 |
| Adipate polyester resin (b) | 3 | 5 | 7 | 15 | 20 |
| JONCRYL 611 (c) | 10 | 10 | 10 | 10 | 10 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 1 | 1 | 1 | 1 | 1 |
| Ease of application | ○ | ◎ | ◎ | ◎ | ○ |
| Coating film strength | ◎ | ◎ | ◎ | ◎ | ○ |
| Gloss | | | | | |
| 10 min. later | ○ | ◎ | ◎ | ◎ | ◎ |
| 4 days later | ○ | ○ | ○ | ○ | ○ |
| Peeling off over time | ○ | ◎ | ◎ | ◎ | ◎ |

In Table 7, the adipate polyester resin was UNIPLEX 670-P. Table 7 clearly shows that excellent effects are obtained if the amount of adipate polyester resin formulated is in a range of 3–20% by weight. It particularly shows that a range of 5–15% by weight is preferred.

TABLE 8

|  | Examples | | | | |
| --- | --- | --- | --- | --- | --- |
|  | 31 | 32 | 33 | 34 | 35 |
| Nitrocellulose ¼ sec (30% IPA) (a) | 10 | 10 | 10 | 10 | 10 |
| Adipate polyester resin (b) | 10 | 10 | 10 | 10 | 10 |
| Methyl methacrylate-butyl acrylate Copolymer (c) | 1 | 8 | 15 | 20 | 25 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 3 | 3 | 3 | 3 | 3 |
| Ease of application | ◎ | ◎ | ◎ | ◎ | ○ |
| Coating film strength | ○ | ◎ | ◎ | ◎ | ◎ |
| Gloss | | | | | |
| 10 min. later | ○ | ◎ | ◎ | ◎ | ◎ |
| 4 days later | ○ | ○ | ○ | ○ | ○ |
| Peeling off over time | ◎ | ◎ | ◎ | ◎ | ○ |

In Table 8 the adipate polyester resin was UNIPLEX 670-P. The methyl methacrylate-butyl acrylate copolymer had a weight average molecular weight of 8,000.

Table 8 clearly shows that excellent effects are obtained if the amount of the methyl acrylate butyl acrylate copolymer formulated is in a range of 1–25% by weight. It particularly shows that a range of 8–20% by weight is preferred.

TABLE 9

|  | Examples | | | | |
|---|---|---|---|---|---|
|  | 36 | 37 | 38 | 39 | 40 |
| Nitrocellulose ¼ sec (30% IPA) (a) | 10 | 10 | 10 | 10 | 10 |
| Adipate polyester resin (b) | 10 | 10 | 10 | 10 | 10 |
| Sucrose benzoate (c) | 0.5 | 3 | 6 | 15 | 25 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 1 | 1 | 1 | 1 | 1 |
| Ease of application | ◉ | ◉ | ◉ | ◉ | ○ |
| Coating film strength | ○ | ◉ | ◉ | ◉ | ◉ |
| Gloss |  |  |  |  |  |
| 10 min. later | ○ | ◉ | ◉ | ◉ | ◉ |
| 4 days later | ○ | ○ | ○ | ○ | ○ |
| Peeling off over time | ◉ | ◉ | ◉ | ◉ | ○ |

In Table 9, the adipate polyester resin was UNIPLEX 670-P. Table 9 clearly shows that excellent effects are obtained if the amount of sucrose benzoate formulated is in a range of 0.5–25% by weight. It particularly shows that a range of 3–15% by weight is preferred.

TABLE 10

|  | Examples | | | | |
|---|---|---|---|---|---|
|  | 41 | 42 | 43 | 44 | 45 |
| Nitrocellulose ¼ sec (30% IPA) (a) | 10 | 10 | 10 | 10 | 10 |
| Adipate polyester resin (b) | 10 | 10 | 10 | 10 | 10 |
| JONCRYL 611 (c) | 0.5 | 3 | 6 | 15 | 25 |
| Acetyltriethyl citrate | 5 | 5 | 5 | 5 | 5 |
| n-Butyl alcohol | 1 | 1 | 1 | 1 | 1 |
| Ethyl acetate | 20 | 20 | 20 | 20 | 20 |
| n-Butyl acetate | Bal | Bal | Bal | Bal | Bal |
| Organically modified clay mineral | Opt | Opt | Opt | Opt | Opt |
| Pearlescent Agent | 2 | 2 | 2 | 2 | 2 |
| Pigment | 1 | 1 | 1 | 1 | 1 |
| Ease of application | ◉ | ◉ | ◉ | ◉ | ○ |
| Coating film strength | ○ | ◉ | ◉ | ◉ | ◉ |
| Gloss |  |  |  |  |  |
| 10 min. later | ○ | ◉ | ◉ | ◉ | ◉ |
| 4 days later | ○ | ○ | ○ | ○ | ○ |
| Peeling off over time | ◉ | ◉ | ◉ | ◉ | ○ |

In Table 10, the adipate polyester resin was UNIPLEX 670-P.

Table 10 clearly shows that excellent effects are obtained if the amount of JONCRYL 611 formulated is in a range of 0.5–25% by weight. It particularly shows that a range of 3–15% by weight is preferred.

Nail enamels for Examples 46–54 were prepared by the usual method as below. All enamels were excellent in ease of application, coating film strength, and gloss and difficult to peel. They all had good drying capability and exerted minimal feeling of compression on the nail.

EXAMPLE 46

Nail Enamel

| (Formulation components) | (Amount formulated) |
|---|---|
| Nitrocellulose ¼ second (30% IPA) | 15% by weight |
| Adipate polyester resin | 5 |
| Methyl methacrylate-butyl acrylate-2-ethylhexyl methacrylate copolymer | 20 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P. The methyl methacrylate-butyl methacrylate-2-ethylhexyl methacrylate copolymer had a weight average molecular weight of 8,000.

EXAMPLE 47

Nail Enamel

| (Formulation components) | (Amount formulated) |
|---|---|
| Nitrocellulose ¼ second (30% IPA) | 15% by weight |
| Adipate polyester resin | 10 |
| Methyl methacrylate-butyl acrylate-2-ethylhexyl methacrylate copolymer | 8 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P. The methyl methacrylate-butyl methacrylate-2-ethylhexyl methacrylate copolymer had a weight average molecular weight of 8,100.

EXAMPLE 48

Nail Enamel

| (Formulation components) | (Amount formulated) |
|---|---|
| Nitrocellulose ½ second (30% IPA) | 10% by weight |
| Adipate polyester resin | 15 |
| Octyl methacrylate-methyl acrylate-methacrylic acid copolymer | 15 |
| Modified alkyd resin | 10 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P. The octyl methacrylate-methyl acrylate-methacrylic acid copolymer had a weight average molecular weight of 8,100.

EXAMPLE 49

Nail Enamel

| (Formulation components) | (Amount formulated) |
|---|---|
| Nitrocellulose ¼ second (30% IPA) | 10% by weight |
| Adipate polyester resin | 5 |
| Methyl methacrylate-butyl acrylate-copolymer | 8 |
| Sucrose benzoate | 3 |
| Toluene sulfonamide | 4 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P. The methyl methacrylate-butyl acrylate copolymer had a weight average molecular weight of 5,000.

EXAMPLE 50

Nail Enamel

| (Formulation components) | (Amount formulated) |
|---|---|
| Nitrocellulose ½ second (30% IPA) | 15% by weight |
| Adipate polyester resin | 10 |
| Sucrose benzoate | 9 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P.

EXAMPLE 51

Nail Enamel

| (Formulation components) | (Amount formulated) |
|---|---|
| Nitrocellulose ¼ second (30% IPA) | 18% by weight |
| Adipate polyester resin | 15 |
| Sucrose benzoate | 15 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

The adipate polyester resin was UNIPLEX 670-P.

EXAMPLE 52

Nail Enamel

| (Formulation components) | (Amount formulated) |
|---|---|
| Nitrocellulose ½ second (30% IPA) | 5% by weight |
| Nitrocellulose ⅛ second (30% IPA) | 12 |
| Adipate polyester resin | 12 |
| Sucrose benzoate | 2 |
| Acetyltriethyl citrate | 5 |
| Pigment | 1 |
| Organically modified clay mineral | optimum |
| n-Butyl alcohol | 0.5 |
| Ethyl acetate | 8.5 |
| n-Butyl acetate | balance |
| Citric acid | optimum |

The adipate polyester resin was UNIPLEX 670-P.

EXAMPLE 53

Nail Enamel

| (Formulation components) | (Amount formulated) |
|---|---|
| Nitrocellulose ½ second (30% IPA) | 5% by weight |
| Nitrocellulose ¹⁄₁₆ second (30% IPA) | 13 |
| Adipate polyester resin | 12 |
| Sucrose benzoate | 2 |
| Acetyltriethyl citrate | 5 |
| Pigment | 1 |
| Organically modified clay mineral | optimum |
| n-Butyl alcohol | 0.5 |
| Ethyl acetate | 8.5 |
| n-Butyl acetate | balance |
| Citric acid | optimum |

The adipate polyester resin was UNIPLEX 670-P.

EXAMPLE 54

Nail Enamel

| (Formulation components) | (Amount formulated) |
|---|---|
| Nitrocellulose ¼ second (30% IPA) | 7% by weight |
| Nitrocellulose ½ second (30% IPA) | 5 |
| Adipate polyester resin (*1) | 8 |
| Alkyl methacrylate-alkyl acrylate Copolymer (*2) | 8 |
| Sucrose benzoate (*3) | 4 |
| Toluene sulfonamide resin | 4 |
| Acetyltriethyl citrate | 5 |
| n-Butyl alcohol | 1 |
| Ethyl acetate | 20 |
| n-Butyl acetate | balance |
| Pigment | 1 |
| Organically modified clay mineral | optimum |

(*1) UNIPLEX 670-P
(*2) JONCRYL 611
(*3) MONOPET SB

EXAMPLE 55

Overcoat

| (Formulation components) | (Amount formulated) |
|---|---|
| Nitrocellulose ½ second (30% IPA) | 12% by weight |
| Adipate polyester resin | 10 |
| Methyl methacrylate-butyl acrylate-copolymer | 10 |
| Sucrose benzoate | 5 |
| Toluene sulfonamide resin | 4 |
| Acetyltriethyl citrate | 5 |
| n-Butyl alcohol | 1 |
| Ethyl acetate | 25 |
| n-Butyl acetate | balance |
| Pigment | 1 |
| Organically modified clay mineral | optimum |

An overcoat was prepared by the usual method. It was excellent in ease of application, coating film strength, and gloss and difficult to peel even over a period of time, and the gloss was not lost. It also had good drying capability and exerted minimal feeling of compression on the nail. Incidentally, the adipate polyester resin was UNIPLEX 670-P. The methyl methacrylate-butyl acrylate copolymer had a weight average molecular weight of 8,100.

EXAMPLE 56

Overcoat

| (Formulation components) | (Amount formulated) |
|---|---|
| Nitrocellulose ½ second (30% IPA) | 12% by weight |
| Adipate polyester resin (*1) | 10 |
| Alkyl methacrylate-alkyl acrylate-Copolymer (*2) | 15 |
| Toluene sulfonamide resin | 4 |
| Acetyltriethyl citrate | 5 |
| n-Butyl alcohol | 1 |
| Ethyl acetate | 25 |
| n-Butyl acetate | balance |
| Pigment | 1 |
| Organically modified clay mineral | optimum |

(*1) UNIPLEX670-P
(*2) JONCRYL 611

An overcoat was prepared by the usual method. It was excellent in ease of application, coating film strength, and gloss and difficult to peel even over a period of time, and the gloss was not lost. It also had good drying capability and exerted minimal feeling of compression on the nail.

EXAMPLE 57

Base Coat

| (Formulation components) | (Amount formulated) |
|---|---|
| Nitrocellulose ¼ second (30% IPA) | 7% by weight |
| Nitrocellulose ½ second (30% IPA) | 5 |
| Adipate polyester resin | 10 |
| Methyl methacrylate-butyl acrylate-copolymer | 7 |
| Sucrose benzoate | 6 |
| Alkyd resin (Glycidyl versatate ester-modified) | 6 |
| Acetyltriethyl citrate | 5 |
| n-Butyl alcohol | 1 |
| Ethyl acetate | 25 |
| n-Butyl acetate | balance |
| Pigment | 1 |
| Organically modified clay mineral | optimum |

A base coat was prepared by the usual method. It was excellent in ease of application, coating film strength, and gloss and difficult to peel even over a period of time, and the gloss was not lost. It also had good drying capability and exerted minimal feeling of compression on the nail. Incidentally, the adipate polyester resin was UNIPLEX 670-P. The methyl methacrylate-butyl acrylate copolymer had a weight average molecular weight of 8,000.

EXAMPLE 58

Base Coat

| (Formulation components) | (Amount formulated) |
|---|---|
| Nitrocellulose ¼ second (30% IPA) | 7% by weight |
| Nitrocellulose ½ second (30% IPA) | 5 |
| Adipate polyester resin (*1) | 10 |
| Sucrose benzoate (*2) | 13 |
| Alkyd resin (Glycidyl versatate ester-modified) | 6 |
| Acetyltriethyl citrate | 5 |
| n-Butyl alcohol | 1 |
| Ethyl acetate | 25 |
| n-Butyl acetate | balance |
| Pigment | 1 |
| Organically modified clay mineral | optimum |

(*1) UNIPLEX 670-P
(*2) MONOPET SB

A base coat was prepared by the usual method. It was excellent in ease of application, coating film strength, and gloss and difficult to peel even over a period of time, and the gloss was not lost. It also had good drying capability and exerted minimal feeling of compression on the nail.

POTENTIAL INDUSTRIAL UTILITY

As described above in details, the present invention can provide a solvent-based nail-care composition which is easy to apply, excellent in the strength of a film (coating film) on the nail and gloss, and difficult to peel even over a period of time and which has a lasting gloss; accordingly, it can be used as a cosmetic preparation.

What is claimed is:

1. A nail-care composition comprising (a) nitrocellulose, (b) neopentyl glycol trimellitate adipate polyester resin, (c) one, two, or more members selected from the group consisting of alkyl methacrylate-alkyl acrylate copolymers, sucrose benzoate, and a polymeric compound having a glass transition temperature of 50–80° C., and (d) a solvent.

2. A nail-care composition as set forth in claim 1, wherein the neopentyl glycol trimellitate adipate polyester resin has an acid value of 10–30 mg KOH/g.

3. A nail-care composition as set forth in claim 1, wherein the alkyl group in the alkyl methacrylate, constituting the alkyl methacrylate-alkyl acrylate-containing copolymer, has 1–8 carbon atoms.

4. A nail-care composition as set forth in claim 1, wherein the alkyl group in the alkyl acrylate, constituting the alkyl methacrylate-alkyl acrylate-containing copolymer, has 1–8 carbon atoms.

5. A nail-care composition as set forth in claim 1, wherein the alkyl methacrylate-alkyl acrylate-containing copolymer as a weight average molecular weight of 1,000–9,000.

6. A nail-care composition as set forth in claim 2, wherein the alkyl group in the alkyl methacrylate, constituting the alkyl methacrylate-alkyl acrylate-containing copolymer, has 1–8 carbon atoms.

7. A nail-care composition as set forth in claim 2, wherein the alkyl group in the alkyl acrylate, constituting the alkyl methacrylate-alkyl acrylate-containing copolymer, has 1–8 carbon atoms.

8. A nail-care composition as set forth in claim 3, wherein the alkyl group in the alkyl acrylate, constituting the alkyl methacrylate-alkyl acrylate-containing copolymer, has 1–8 carbon atoms.

9. A nail-care composition as set forth in claim 2, wherein the alkyl methacrylate-alkyl acrylate-containing copolymer as a weight average molecular weight of 1,000–9,000.

10. A nail-care composition as set forth in claim 3, wherein the alkyl methacrylate-alkyl acrylate-containing copolymer as a weight average molecular weight of 1,000–9,000.

11. A nail-care composition as set forth in claim 4, wherein the alkyl methacrylate-alkyl acrylate-containing copolymer as a weight average molecular weight of 1,000–9,000.

* * * * *